(12) United States Patent
Lemersal et al.

(10) Patent No.: US 10,912,481 B2
(45) Date of Patent: Feb. 9, 2021

(54) BIOIMPEDANCE MEASUREMENT SYSTEM CALIBRATION

(71) Applicant: PHILIPS HEALTHCARE INFORMATICS INC., Cambridge, MA (US)

(72) Inventors: Donald Bernard Lemersal, San Diego, CA (US); Jed Wilson, San Diego, CA (US)

(73) Assignee: Koninklijke Philips N.V., Eindhoven (NL)

( * ) Notice: Subject to any disclaimer, the term of this patent is extended or adjusted under 35 U.S.C. 154(b) by 386 days.

(21) Appl. No.: 15/233,819

(22) Filed: Aug. 10, 2016

(65) Prior Publication Data
US 2018/0042488 A1 Feb. 15, 2018

(51) Int. Cl.
*A61B 5/053* (2006.01)
*A61B 5/00* (2006.01)
(Continued)

(52) U.S. Cl.
CPC ............ *A61B 5/053* (2013.01); *A61B 5/0205* (2013.01); *A61B 5/02444* (2013.01);
(Continued)

(58) Field of Classification Search
CPC ... A61B 5/0205; A61B 5/6826; A61B 5/6898; A61B 5/7225; A61B 5/7278;
(Continued)

(56) References Cited

U.S. PATENT DOCUMENTS 7,228,170 B2   6/2007  Zhu et al.
8,412,317 B2 * 4/2013  Mazar ................. A61B 5/0531
                                                       600/547
(Continued)

FOREIGN PATENT DOCUMENTS

EP          2767230 A1    8/2014

OTHER PUBLICATIONS

Macias R.M., "Towards Wearable Spectroscopy Bioimpedance Applications: Power Management for a Battery Driven Impedance Meter," May 2009, 74 pages.
(Continued)

*Primary Examiner* — Devin B Henson (57) ABSTRACT

Techniques are disclosed for measuring bioimpedance of a biological object with an alternating current (AC) source, a pair of electrodes, a reference load, a switching arrangement switchable between a first switch condition and a second switch condition, and measuring electronics. When the switching arrangement is in the first switch condition, the AC source is applied across the reference load and a group delay of the measuring electronics is determined. When the switching arrangement is in the second switch condition, and the pair of electrodes is in contact with the biological object, a voltage waveform based on the AC source being applied across the pair of electrodes is measured and a calibrated voltage waveform is determined, the calibrated voltage waveform being corrected for the group delay. The bioimpedance value of the biological object is determined based on the calibrated voltage waveform.

28 Claims, 4 Drawing Sheets

(51) Int. Cl.
    *A61B 5/024*        (2006.01)
    *A61B 5/0205*      (2006.01)
    *A61B 5/145*        (2006.01)
    *A61B 5/04*         (2006.01)
    *A61B 5/0428*      (2006.01)
    *A61B 5/021*       (2006.01)
    *A61B 5/0245*      (2006.01)

(52) U.S. Cl.
    CPC ........ *A61B 5/14532* (2013.01); *A61B 5/6826* (2013.01); *A61B 5/6898* (2013.01); *A61B 5/7225* (2013.01); *A61B 5/7278* (2013.01); *A61B 5/021* (2013.01); *A61B 5/0245* (2013.01); *A61B 5/04004* (2013.01); *A61B 5/0428* (2013.01); *A61B 5/14542* (2013.01); *A61B 2560/0223* (2013.01); *A61B 2562/0209* (2013.01)

(58) Field of Classification Search
    CPC ....... A61B 5/021; A61B 5/053; A61B 5/0535; A61B 2560/0223
    See application file for complete search history.

(56) References Cited

U.S. PATENT DOCUMENTS

| | | | |
|---|---|---|---|
| 9,220,420 B2* | 12/2015 | Weinstein | A61B 5/0028 |
| 2001/0010467 A1 | 8/2001 | Oguma et al. | |
| 2007/0043303 A1 | 2/2007 | Osypka et al. | |
| 2007/0210786 A1* | 9/2007 | Allen | A61B 5/0002 324/76.53 |
| 2011/0208458 A1 | 8/2011 | Pinter et al. | |
| 2013/0172775 A1 | 7/2013 | Ozawa | |
| 2014/0088902 A1 | 3/2014 | Osypka et al. | |
| 2015/0031971 A1* | 1/2015 | Lisogurski | A61B 5/14552 600/324 |

OTHER PUBLICATIONS

International Search Report and Written Opinion—PCT/US2017/039551—ISA/EPO—dated Sep. 21, 2017.
International Preliminary Report on Patentability—PCT/US2017/039551—ISA/EPO—dated Oct. 8, 2018.

* cited by examiner

BIOIMPEDANCE MEASUREMENT SYSTEM CALIBRATION

TECHNICAL FIELD

This disclosure relates to a bioimpedance measurement system, and more particularly to improved techniques for calibrating the bioimpedance measurement system.

DESCRIPTION OF THE RELATED TECHNOLOGY

Bioelectrical impedance (bioimpedance) measurements afford a non-invasive means of obtaining physiological parameters including vital signs and other diagnostic information regarding a patient's medical condition. For example, arterial blood pressure data may be obtained by means of a bioimpedance measuring device. Advantages of such devices may include avoidance of a need for conventional upper arm pressure cuffs, and an ability to obtain blood pressure information more quickly and/or at more frequent intervals, more conveniently and with less patient inconvenience and discomfort.

In a typical bioimpedance measurement scheme, a small alternating current (AC) excitation source is coupled with a pair of electrodes. During a bioimpedance measurement, the electrodes are brought into contact with a biological object to be tested (e.g., a patient's forearm or finger). The biological object may be electrically modeled as a 2R-1C circuit. Measuring electronics are configured to determine, from voltage variations at the electrodes, a bioimpedance of the biological object.

Bioimpedance is a complex quantity, that is, bioimpedance includes reactance as well as resistance. As a result, in order to obtain an accurate bioimpedance value during a measurement procedure, it is necessary to measure in phase with the AC excitation source. In the absence of the presently disclosed techniques, because of unpredictable and varying group delay in the measuring electronics, "in phase" measurements are difficult to reliably achieve. In addition, a change in initial group delay may arise from temperature variations (due to changes in ambient conditions and Joule heating of measuring electronics) and equipment age, among other causes.

SUMMARY

The systems, methods and devices of this disclosure each have several innovative aspects, no single one of which is solely responsible for the desirable attributes disclosed herein.

One innovative aspect of the subject matter described in this disclosure relates to an apparatus that includes an alternating current (AC) source, a pair of electrodes, a reference load, a switching arrangement switchable between a first switch condition and a second switch condition, and measuring electronics. In response to the switching arrangement being in the first switch condition, the AC source is applied across the reference load and the apparatus performs a first operation with respect to a resulting first voltage waveform across the reference load. In response to the switching arrangement being in the second switch condition, the AC source is applied across the pair of electrodes and the apparatus performs a second operation with respect to a resulting second voltage waveform across the pair of electrodes.

In some examples, when the pair of electrodes is in contact with a biological object, the apparatus may be operable to determine a bioimpedance value of the biological object. In some examples, the first operation may include determining a group delay of the measuring electronics, the second operation may include determining a calibrated second voltage waveform, the calibrated second voltage waveform being corrected for the group delay; and the apparatus may be operable to determine the bioimpedance value of the biological object from the calibrated second voltage waveform. In some examples, the biological object is an anatomical feature of a subject and the apparatus may be configured to determine, from the bioimpedance value, one or more physiological parameters of the subject. In some examples, the one or more physiological parameters may include arterial blood pressure, heart rate, oxygen levels or any combination thereof. In some examples, the anatomical feature may be a finger or other body part or portion thereof.

In some examples, the reference load may exhibit negligible reactance at frequencies less than 10 MHz.

In some examples, at least one of the first operation and the second operation may include detecting a peak voltage and the apparatus may be configured to determine a group delay of the measuring electronics based on the detected peak voltage.

In some examples, the measuring electronics may include an analog to digital converter disposed in series with and between analog circuitry and a processor.

In some examples, the apparatus may include a processor configured to control the switching arrangement, and to execute the first operation and the second operation. In some examples, the processor may be configured to: set the switching arrangement to the first switch condition; execute the first operation such that a group delay of the measuring electronics is determined from the resulting first voltage waveform; set the switching arrangement to the second switch condition; and execute the second operation such that a calibrated second voltage waveform across the pair of electrodes is determined, the calibrated second voltage waveform being corrected for the group delay.

In some examples, the apparatus may include one or more of a sensor, a mobile device, a wearable device, or a medical device.

According to some implementations, in a method for determining a bioimpedance value of a biological object using a bioimpedance measurement system, the bioimpedance measurement system including measuring electronics, the method includes determining a group delay of the measuring electronics based on an alternating current (AC) source being applied across a reference load of the bioimpedance measurement system, determining a voltage waveform based on the AC source being applied across a pair of electrodes of the bioimpedance measurement system, when the pair of electrodes is in contact with the biological object, calibrating the voltage waveform by correcting for the group delay, and determining the bioimpedance value of the biological object based on the calibrated voltage waveform.

In some examples, the biological object may be an anatomical feature of a subject and the bioimpedance measurement system is configured to determine, from the bioimpedance value, a physiological parameter of the subject. In some examples, the physiological parameter may include one or more of arterial blood pressure, heart rate, and oxygen levels. In some examples, the anatomical feature may be a finger or other body part or portion thereof.

In some examples, the reference load may exhibit negligible reactance at frequencies less than 10 MHz.

In some examples, the measuring electronics may include an analog to digital converter disposed in series with and between analog circuitry and a digital signal processor.

According to some implementations, an apparatus for measuring bioimpedance includes an alternating current (AC) source, a pair of electrodes, a reference load, a switching arrangement switchable between a first switch condition and a second switch condition, measuring electronics, and means for: setting the switching arrangement to the first switch condition wherein the AC source is applied so as to produce a resulting first voltage waveform across the reference load; determining a group delay of the measuring electronics from the resulting first voltage waveform; setting the switching arrangement to a second switch condition wherein the AC source is applied across the pair of electrodes, the pair of electrodes being in contact with a biological object; and determining a calibrated second voltage waveform across the pair of electrodes, the calibrated second voltage waveform being corrected for the group delay.

In some examples, the apparatus may be operable to determine, from the calibrated second voltage waveform, a bioimpedance value of the biological object. In some examples, the biological object may be an anatomical feature of a subject and the apparatus is configured to determine, from the bioimpedance value, a physiological parameter of the subject. In some examples, the physiological parameter may include one or more of arterial blood pressure, heart rate, and oxygen levels. In some examples, the anatomical feature may be a finger or other body part or portion thereof.

In some examples, the measuring electronics may include an analog to digital converter disposed in series with and between analog circuitry and a processor.

According to some implementations, in a non-transitory computer readable medium having software stored thereon, the software including instructions for causing a bioimpedance measurement system to execute a process for determining a bioimpedance value of a biological object, the bioimpedance measurement system including measuring electronics, the process includes: determining a group delay of the measuring electronics based on an alternating current (AC) source being applied across a reference load of the bioimpedance measurement system; determining a voltage waveform based on the AC source being applied across a pair of electrodes of the bioimpedance measurement system, when the pair of electrodes is in contact with the biological object; calibrating the voltage waveform by correcting for the group delay; and determining the bioimpedance value of the biological object based on the calibrated voltage waveform.

BRIEF DESCRIPTION OF THE DRAWINGS

Details of one or more implementations of the subject matter described in this specification are set forth in this disclosure and the accompanying drawings. Other features, aspects, and advantages will become apparent from a review of the disclosure. Note that the relative dimensions of the drawings and other diagrams of this disclosure may not be drawn to scale. The sizes, thicknesses, arrangements, materials, etc., shown and described in this disclosure are made only by way of example and should not be construed as limiting. Like reference numbers and designations in the various drawings indicate like elements.

DETAILED DESCRIPTION

Details of one or more implementations of the subject matter described in this specification are set forth in this disclosure, which includes the description and claims in this document, and the accompanying drawings. Other features, aspects and advantages will become apparent from a review of the disclosure. Note that the relative dimensions of the drawings and other diagrams of this disclosure may not be drawn to scale. The sizes, thicknesses, arrangements, materials, etc., shown and described in this disclosure are made only by way of example and should not be construed as limiting.

The present inventors have developed improved bioimpedance measurement techniques. The systems, methods and devices of the disclosure each have several innovative aspects, no single one of which is solely responsible for the desirable attributes disclosed herein. The disclosed techniques enable an accurate bioimpedance measurement to be taken notwithstanding unpredictable group delay in the measuring electronics. Advantageously, the disclosed techniques may be implemented while adding little in the way of additional cost or complexity to a sampled measurement system.

Figure 1:
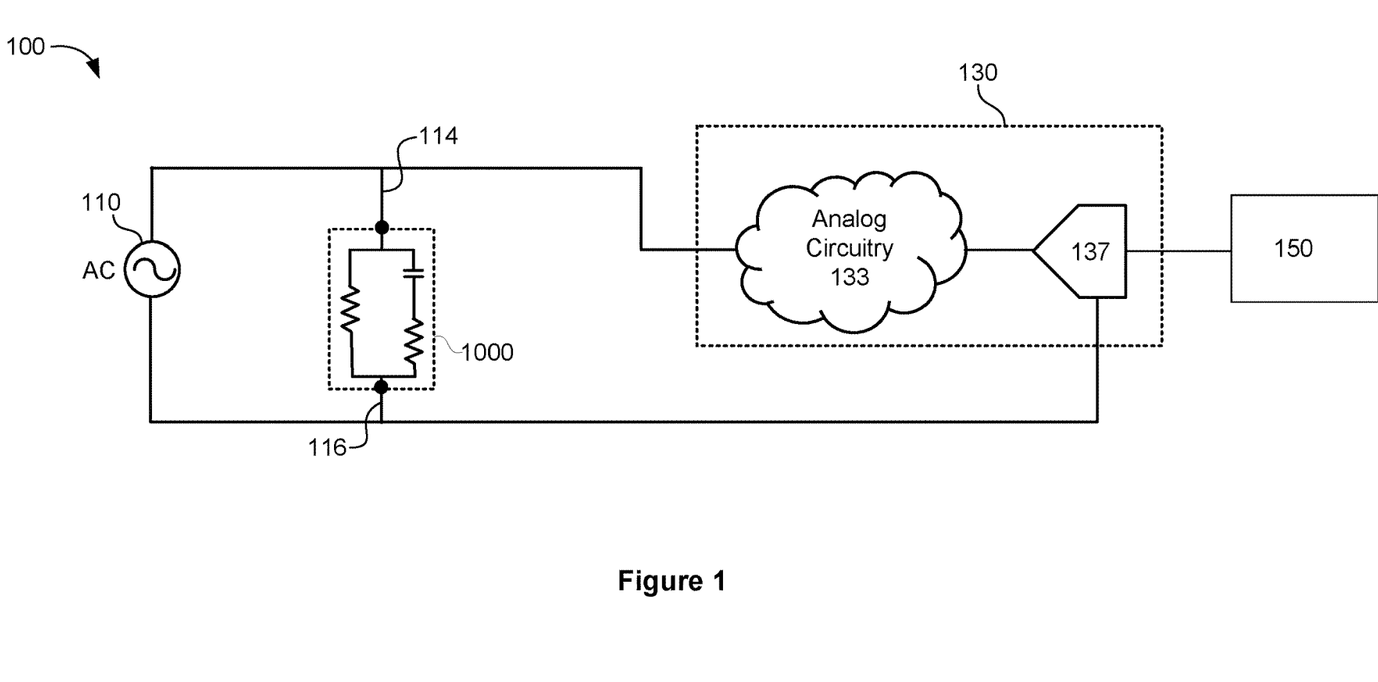
FIG. 1 illustrates a bioimpedance measurement system.

FIG. 1 illustrates a bioimpedance measurement system. A bioimpedance measurement system 100 includes an alternating current (AC) source 110 coupled with electrodes 114 and 116. During a bioimpedance measurement, the electrodes 114 and 116 are in contact with a biological object 1000 to be tested. The biological object 1000 may be an anatomical feature of a subject (e.g., a human patient, or an animal undergoing examination) such as a finger or other body part or portion thereof. In FIG. 1, the biological object 1000 is depicted schematically as an electrically modeled 2R-1C circuit. Measuring electronics 130 (in the illustrated example, analog circuitry 133 and analog/digital converter (ADC) 137) and digital signal processing (DSP) 150 are configured to determine, from voltage variations at the electrodes 114 and 116, electrical impedance of the biological object 1000. In the absence of the presently disclosed techniques, because of unpredictable and varying group delay in the measuring electronics, particularly in analog circuitry 133, "in phase" measurements are difficult to reliably achieve. As a result, an accurate determination of absolute bioimpedance using the arrangement illustrated in FIG. 1 may be impossible.

Figure 2:
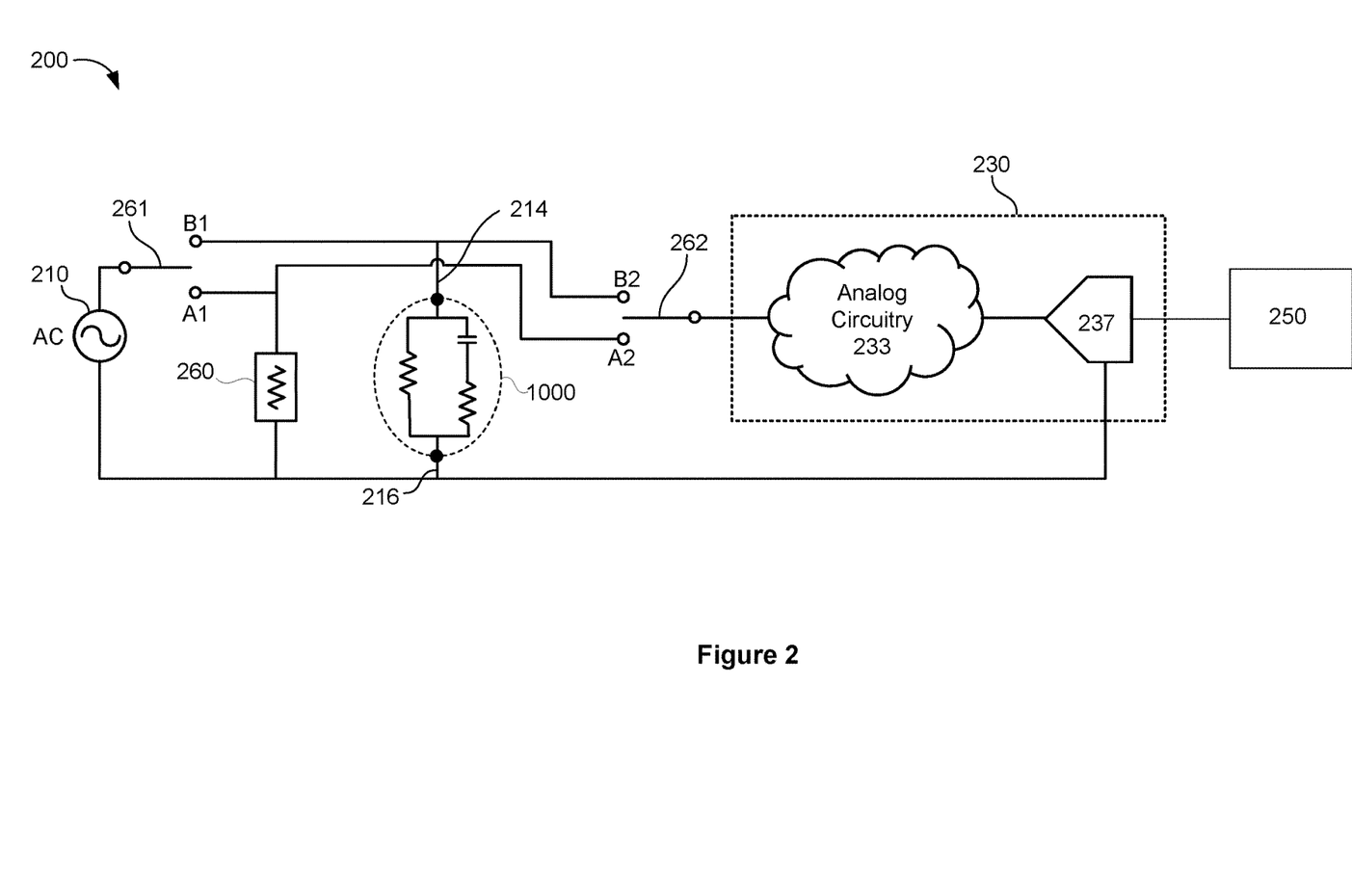
FIG. 2 illustrates a bioimpedance measuring system according to an implementation.

According to the presently disclosed techniques, a load, having a real constant impedance (i.e. one that excludes all but negligible reactive components), referred to herein as the "reference load", is included in a bioimpedance measuring system. FIG. 2 illustrates a bioimpedance measuring system, according to an implementation. The bioimpedance measuring system may be configured as a sensor, a mobile device, a wearable device, or a medical device, for example. In the illustrated implementation, a bioimpedance measuring system 200 includes a reference load 260 that is selectively coupled, by way of switches 261 and 262 with an AC source 210 and with measuring electronics 230. The reference load 260 may be disposed, for example, proximate to the biological object 1000. When switches 261 and 262 are set, respectively, to position "A1" and "A2", the reference load 260 is under measurement. Advantageously, the reference load 260 may be configured so as to exhibit negligible reactance at a frequency of interest. For example, the reference load may be configured so as to exhibit a complex impedance having a reactive component that is negligible at frequencies less than 10 MHz. As a result, the bioimpedance measuring system 200, using a digital signal processor (DSP) 250 or other electronic circuits (not illustrated) such as, for example, a general purpose processor, central processing unit (CPU), graphic processing unit (GPU) or microcontroller, may be configured to calibrate the 0° phase point by determining the group delay exhibited by the analog circuitry 233 and the ADC 237. When switches 261 and 262 are set, respectively, to positions "B1" and "B2", and electrodes 214 and 216 are in contact with the biological object 1000, the DSP 250 may be configured to process a voltage across the electrode probes 214 and 216 so as to determine bioimpedance of the biological object 1000. For example, when switches 261 and 262 are set to respective positions A1 and A2, the DSP 250 may be configured to determine a group delay of the measuring electronics 230. When switches 261 and 262 are set to respective positions B1 and B2, the DSP 250 may be configured to make a correction for the group delay, and determine a bioimpedance value of the biological object 1000.

The switches 261 and 262 may be referred to herein as a switching arrangement. The switching arrangement may be switchable between a first switch condition and a second switch condition. The switches may be controlled directly by an operator or be controlled automatically or semi-automatically by measuring electronics 230, DSP 250 or other electronic circuits. In the first switch condition (in which switches 261 and 262 are set, respectively, to position "A1" and "A2"), the AC source 210 is applied across the reference load 260. A resulting voltage waveform (the "first voltage waveform") may be processed by the measuring electronics 230 and the DSP 250 to determine (as a result of a "first operation") the group delay of the measuring electronics 230. In the second switch condition (in which switches 261 and 262 are set, respectively, to position "B1" and "B2"), the AC source 210 is applied across the pair of electrodes 214 and 216. When the pair of electrodes 214 and 216 is in contact with the biological object 1000, a different resulting voltage waveform (the "second voltage waveform") may be processed by the measuring electronics 230 and the DSP 250 so as to determine (as a result of a "second operation") a calibrated second voltage waveform, the calibrated second voltage waveform being corrected for the group delay of the measuring electronics 230. In an implementation, the first operation may include detecting a peak voltage of the first voltage waveform and/or the second operation may include detecting a peak voltage of the second voltage waveform. The bioimpedance measuring system 200 may be configured to determine the group delay of the measuring electronics based on the detected peak voltage(s).

In an implementation, DSP 250 may execute an algorithm to determine a group delay between the 0° degree phase point of the AC source 210, and the 0° degree phase point phase of a measured voltage waveform. The 0° degree phase point may be regarded as occurring when the measured voltage is at its peak. In an implementation, the group delay may be determined when the AC source 210 is applied across the reference load 260, which may be a substantially non-reactive (i.e., almost a purely resistive) impedance.

A voltage waveform may be determined when the AC source 210 is applied across the electrodes 214 and 216, the electrodes being in contact with the biological object 1000. The voltage waveform may then be calibrated by correcting for the group delay thereby eliminating any phase-shifting effect of the analog circuitry 283, electrodes 214 and 216, or anything else that is in the signal path.

In an implementation, the DSP 250 may be configured to determine the bioimpedance value of the biological object 1000 from the calibrated second voltage waveform. In an implementation, the biological object 1000 may be an anatomical feature (body part or portion thereof) of a subject (human or animal) and the apparatus 200 may be configured to determine, from the bioimpedance value, a physiological parameter of the subject. For example, arterial blood pressure, heart rate, and oxygen levels may be correlated with the determined bioimpedance value. The anatomical feature may be a finger or other appendage or extremity of a patient, for example.

Figure 3:
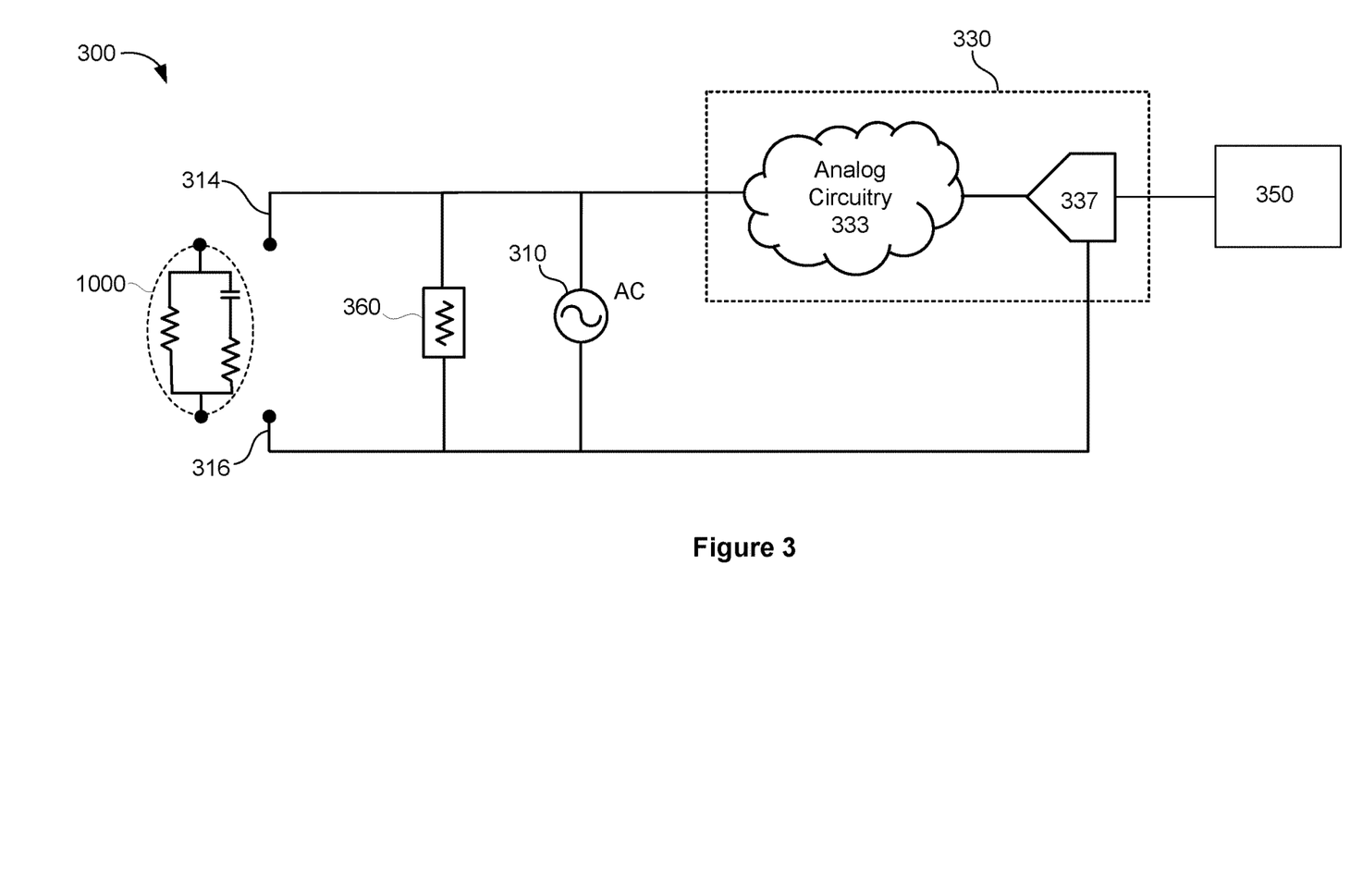
FIG. 3 illustrates an example of a method for determining a bioimpedance value of a biological object, according to an implementation.

FIG. 3 illustrates a bioimpedance measuring system, according to another implementation. In the illustrated implementation, a bioimpedance measuring system 300 includes a reference load 360 that is coupled with an AC source 310 and with measuring electronics 330. The reference load 360 may be disposed, for example, proximate to electrodes 314 and 316 that are configured to interface with biological object 1000. When electrodes 314 and 316 are not in contact with biological object 1000, only the reference load 360 is under measurement. Advantageously, the reference load 360 may be configured so as to exhibit negligible reactance at a frequency of interest. For example, the reference load may be configured so as to exhibit a complex impedance having a reactive component that is negligible at frequencies less than 10 MHz. As a result, the bioimpedance measuring system 300, using a digital signal processor (DSP) 350 or other electronic circuits (not illustrated) may be configured to calibrate the 0° phase point by determining the group delay exhibited by the analog circuitry 333 and the ADC 337.

When electrodes 314 and 316 are in contact with the biological object 1000, the DSP 350 may be configured to process a voltage across the electrode probes 314 and 316 so as to determine bioimpedance of the biological object 1000. More particularly, when electrodes 314 and 316 are not in contact with the biological object 1000, the DSP 350 may be configured to determine a group delay of the measuring electronics 330. When electrodes 314 and 316 are in contact with the biological object 1000, the DSP 250 may be configured to make a correction for the group delay and for the known impedance of the reference load 360 and determine a bioimpedance value of the biological object 1000.

Relative to the implementation illustrated in FIG. 2, the bioimpedance measuring system 300 simplifies the switching arrangement. Instead of physical switches 261 and 262, the switching arrangement is switchable between a first condition (where the AC source 310 is not coupled with the biological object 1000) and a second condition (where the AC source 310 is coupled with the biological object 1000) by bringing the electrodes 314 and 316 into contact with the biological object 1000.

Figure 4:
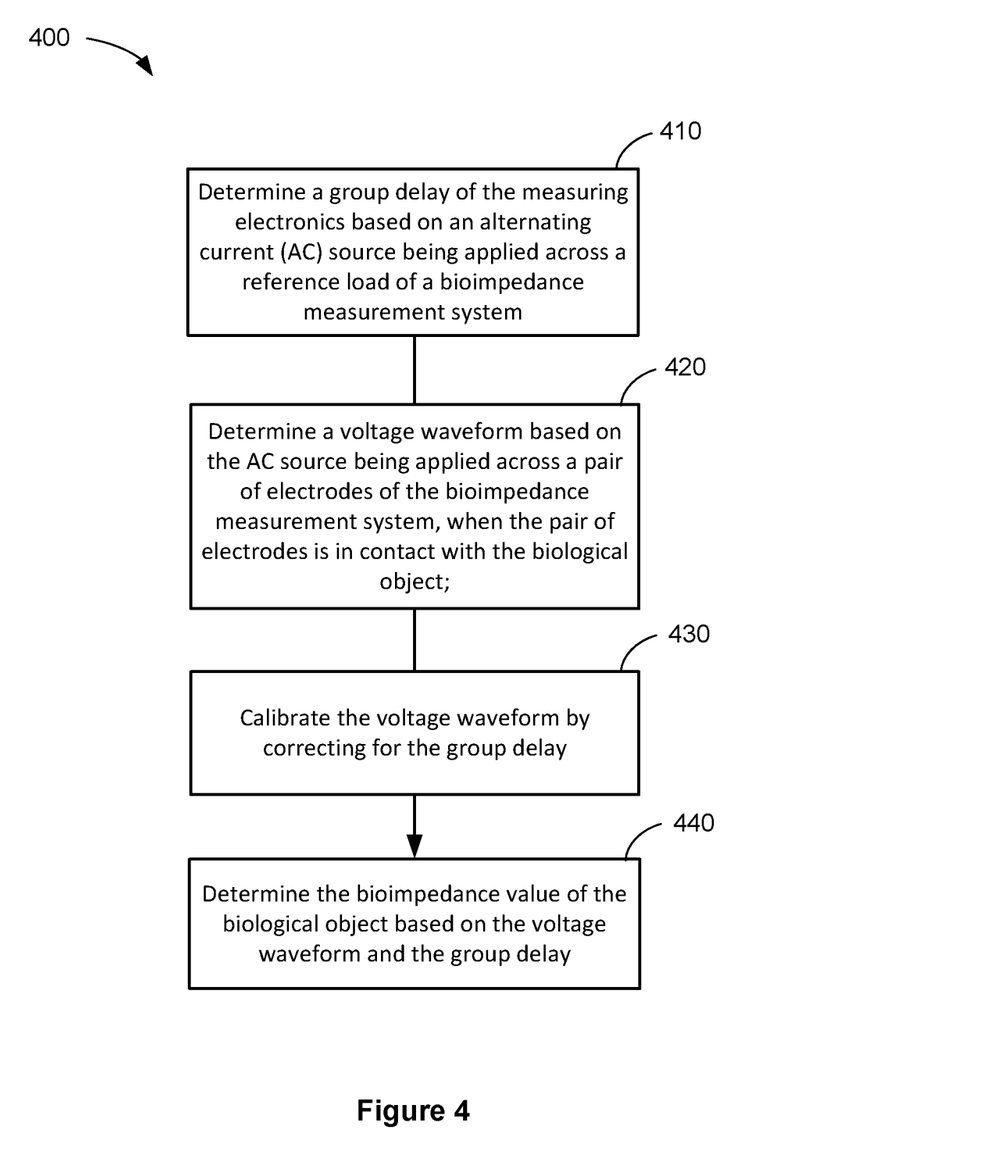
FIG. 4 illustrates an example of a method for determining a bioimpedance value of a biological object, according to an implementation.

FIG. 4 illustrates an example of a method for determining a bioimpedance value of a biological object, according to an implementation. As described hereinabove, the method may be executed using a bioimpedance measurement system that includes an alternating current source, measuring electronics, a reference load, and a pair of electrodes. In the illustrated implementation, method 400 includes a block 410 for determining a group delay of the measuring electronics based on the alternating current (AC) source being applied across the reference load.

The method proceeds, at block 420, with determining a voltage waveform based on the AC source being applied across a pair of electrodes of the bioimpedance measurement system, when the pair of electrodes is in contact with the biological object. In some use cases, block 420 may always be immediately preceded by block 410. In some use cases, however, block 410 may be executed only once, during, for example, an initial set-up phase of a measurement session followed by a series of repetitive executions of block 420.

The method proceeds, at block 430, with calibrating the voltage waveform by correcting for the group delay.

The method concludes, at block 440, with determining the bioimpedance value of the biological object based on the voltage waveform and the group delay.

Thus, improved bioimpedance measurement techniques have been disclosed. The disclosed techniques enable the bioimpedance measurement to be accurate not only in the relative sense (i.e. how bioimpedance is changing vs. time) but accurate in the absolute sense, which allows for a simpler determination of various medical properties such as blood pressure. Advantageously, the disclosed techniques may be implemented while adding little in the way of additional cost or complexity to a sampled measurement system.

It will be appreciated that a number of alternative configurations and fabrication techniques may be contemplated.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor or any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also can be implemented as one or more computer programs, i.e., one or more modules of computer program instructions, encoded on a computer storage media for execution by or to control the operation of data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module which may reside on a computer-readable medium. Computer-readable media include both computer storage media and communication media including any medium that can be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein. Additionally, as a person having ordinary skill in the art will readily appreciate, the terms "upper" and "lower", "top" and "bottom", "front" and "back", and "over", "on", "under" and "underlying" are sometimes used for ease of describing the figures and indicate relative positions corresponding to the orientation of the figure on a properly oriented page, and may not reflect the proper orientation of the device as implemented.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

What is claimed is:

1. An apparatus comprising:
   an alternating current (AC) source;
   a pair of electrodes wherein, when the pair of electrodes is in contact with a biological object, the apparatus is operable to determine a bioimpedance value of the biological object;
   a reference load;
   a switching arrangement switchable between a first switch condition and a second switch condition; and
   measuring electronics, wherein:
      there is a single measuring input to the measuring electronics;
      in response to the switching arrangement being in the first switch condition, the AC source is applied across the reference load and the apparatus performs a first operation with respect to a resulting first voltage waveform across the reference load;
      in response to the switching arrangement being in the second switch condition, the AC source is applied across the pair of electrodes and the apparatus performs a second operation with respect to a resulting second voltage waveform across the pair of electrodes;
      at least one of the first operation and the second operation includes detecting a peak voltage;
      the apparatus is configured to determine a group delay of the measuring electronics based on determining the group delay between a zero-degree phase point of the AC source and a zero-degree phase point of the resulting first voltage waveform where the zero-degree phase point of the resulting first voltage waveform is based on the detected peak voltage;
      the reference load is located between the switching arrangement and ground, where the reference load is permanently connected to ground; and
      the electrode pair is located between the switching arrangement and ground, with one electrode of the pair of electrodes connected to the switching arrangement and one electrode of the pair of electrodes permanently connected to ground.

2. The apparatus of claim 1, wherein: the first operation includes determining the group delay of the measuring electronics; the second operation includes determining a calibrated second voltage waveform, the calibrated second voltage waveform being corrected for the group delay; and the apparatus is operable to determine the bioimpedance value of the biological object from the calibrated second voltage waveform.

3. The apparatus of claim 2, wherein the biological object is an anatomical feature of a subject and the apparatus is configured to determine, from the bioimpedance value, one or more physiological parameters of the subject.

4. The apparatus of claim 3, wherein the one or more physiological parameters includes arterial blood pressure, heart rate, oxygen levels or any combination thereof.

5. The apparatus of claim 3, wherein the anatomical feature is a finger or other appendage.

6. The apparatus of claim 1, wherein the reference load exhibits negligible reactance at frequencies less than 10 MHz.

7. The apparatus of claim 1, wherein the measuring electronics includes an analog to digital converter disposed in series with and between analog circuitry and a processor.

8. The apparatus of claim 1, further comprising a processor configured to control the switching arrangement, and to execute the first operation and the second operation.

9. The apparatus of claim 8, wherein the processor is configured to:
   set the switching arrangement to the first switch condition;
   execute the first operation such that the group delay of the measuring electronics is determined from the resulting first voltage waveform;
   set the switching arrangement to the second switch condition; and
   execute the second operation such that a calibrated second voltage waveform across the pair of electrodes is determined, the calibrated second voltage waveform being corrected for the group delay.

10. The apparatus of claim 1, wherein the apparatus includes one or more of a sensor, a mobile device, a wearable device, or a medical device.

11. A method for determining a bioimpedance value of a biological object using a bioimpedance measurement system, the bioimpedance measurement system including measuring electronics, the method comprising:
   determining a group delay of the measuring electronics based on detecting a peak voltage of a first voltage waveform that results from an alternating current (AC) source being applied across a reference load of the bioimpedance measurement system, wherein determining the group delay comprises determining the group delay between a zero-degree phase point of the AC source and a zero-degree phase point of the first voltage waveform where the zero-degree phase point of the first voltage waveform is based on the peak voltage of the first voltage waveform;
   determining a second voltage waveform based on the AC source being applied across a pair of electrodes of the bioimpedance measurement system, when the pair of electrodes is in contact with the biological object;
   calibrating the second voltage waveform by correcting for the group delay; and
   determining the bioimpedance value of the biological object based on the calibrated second voltage waveform;
   wherein:
   there is a single measuring input to the measuring electronics;
   the bioimpedance measurement system comprises a switching arrangement switchable between a first switch condition and a second switch condition, wherein when the switching arrangement is in the first switch condition the AC source is applied across the reference load, and wherein when the switching arrangement is in the second switch condition the AC source is applied across the pair of electrodes;

the reference load is located between the switching arrangement and ground, where the reference load is permanently connected to ground; and the electrode pair is located between the switching arrangement and ground, with one electrode of the pair of electrodes connected to the switching arrangement and one electrode of the pair of electrodes permanently connected to ground.

12. The method of claim 11, wherein the biological object is an anatomical feature of a subject and the bioimpedance measurement system is configured to determine, from the bioimpedance value, a physiological parameter of the subject.

13. The method of claim 12 wherein the physiological parameter includes one or more of arterial blood pressure, heart rate, and oxygen levels.

14. The method of claim 12 wherein the anatomical feature is a finger or other appendage.

15. The method of claim 11, wherein the reference load exhibits negligible reactance at frequencies less than 10 MHz.

16. The method of claim 11, wherein the measuring electronics includes an analog to digital converter disposed in series with and between analog circuitry and a digital signal processor.

17. An apparatus for measuring bioimpedance, the apparatus comprising:
an alternating current (AC) source;
a pair of electrodes wherein, when the pair of electrodes is in contact with a biological object, the apparatus is operable to determine a bioimpedance value of the biological object;
a reference load;
a switching arrangement switchable between a first switch condition and a second switch condition;
measuring electronics, wherein there is a single measuring input to the measuring electronics; and
electronic means for:
setting the switching arrangement to the first switch condition wherein the AC source is applied so as to produce a resulting first voltage waveform across the reference load;
detecting a peak voltage of a first voltage waveform;
determining a group delay of the measuring electronics based on determining the group delay between a zero-degree phase point of the AC source and a zero-degree phase point of the first voltage waveform where the zero-degree phase point of the first voltage waveform is based on the peak voltage of the first voltage waveform;
setting the switching arrangement to a second switch condition wherein the AC source is applied across the pair of electrodes, the pair of electrodes being in contact with a biological object; and
determining a calibrated second voltage waveform across the pair of electrodes, the calibrated second voltage waveform being corrected for the group delay;
wherein:
the reference load is located between the switching arrangement and ground, where the reference load is permanently connected to ground; and the electrode pair is located between the switching arrangement and ground, with one electrode of the pair of electrodes connected to the switching arrangement and one electrode of the pair of electrodes permanently connected to ground.

18. The apparatus of claim 17, wherein the apparatus is operable to determine, from the calibrated second voltage waveform, a bioimpedance value of the biological object.

19. The apparatus of claim 18, wherein the biological object is an anatomical feature of a subject and the apparatus is configured to determine, from the bioimpedance value, a physiological parameter of the subject.

20. The apparatus of claim 19, wherein the physiological parameter includes one or more of arterial blood pressure, heart rate, and oxygen levels.

21. The apparatus of claim 19, wherein the anatomical feature is a finger or other appendage.

22. The apparatus of claim 17, wherein the reference load exhibits negligible reactance at frequencies less than 10 MHz.

23. The apparatus of claim 17, wherein the measuring electronics includes an analog to digital converter disposed in series with and between analog circuitry and a processor.

24. A non-transitory computer readable medium having software stored thereon, the software including instructions for causing a bioimpedance measurement system to execute a process for determining a bioimpedance value of a biological object, the bioimpedance measurement system including measuring electronics, the process comprising:
determining a group delay of the measuring electronics based on detecting a peak voltage of a first voltage waveform that results from an alternating current (AC) source being applied across a reference load of the bioimpedance measurement system, wherein determining the group delay comprises determining the group delay between a zero-degree phase point of the AC source and a zero-degree phase point of the first voltage waveform where the zero-degree phase point of the first voltage waveform is based on the peak voltage of the first voltage waveform;
determining a second voltage waveform based on the AC source being applied across a pair of electrodes of the bioimpedance measurement system, when the pair of electrodes is in contact with the biological object;
calibrating the second voltage waveform by correcting for the group delay; and determining the bioimpedance value of the biological object based on the calibrated second voltage waveform;
wherein:
there is a single measuring input to the measuring electronics;
the bioimpedance measurement system comprises a switching arrangement switchable between a first switch condition and a second switch condition, wherein when the switching arrangement is in the first switch condition the AC source is applied across the reference load, and wherein when the switching arrangement is in the second switch condition the AC source is applied across the pair of electrodes;
the reference load is located between the switching arrangement and ground, where the reference load is permanently connected to ground; and
the electrode pair is located between the switching arrangement and ground, with one electrode of the pair of electrodes connected to the switching arrangement and one electrode of the pair of electrodes permanently connected to ground.

25. The computer readable medium of claim 24, wherein the biological object is an anatomical feature of a subject and the bioimpedance measurement system is configured to determine, from the bioimpedance value, a physiological parameter the subject.

26. The computer readable medium of claim 25 wherein the physiological parameter includes one or more of arterial blood pressure, heart rate, and oxygen levels.

27. The computer readable medium of claim 25 wherein the subject is a human and the anatomical feature is a finger or other appendage of the human.

28. The computer readable medium of claim 24, wherein the measuring electronics includes an analog to digital converter disposed in series with and between analog circuitry and a digital signal processor.

* * * * *